United States Patent
Srinivas et al.

(10) Patent No.: US 7,405,319 B2
(45) Date of Patent: Jul. 29, 2008

(54) PROCESS FOR THE PREPARATION OF CARBAMATES

(75) Inventors: Darbha Srinivas, Maharashtra (IN); Rajendra Srivastava, Maharashtra (IN); Paul Ratnasamy, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 11/437,859

(22) Filed: May 22, 2006

(65) Prior Publication Data

US 2007/0270605 A1    Nov. 22, 2007

(51) Int. Cl.
*C07C 269/00* (2006.01)
*C07C 259/00* (2006.01)

(52) U.S. Cl. .......................... 560/24; 560/160; 560/157

(58) Field of Classification Search ................. 564/132; 560/24, 115, 157, 160
See application file for complete search history.

(56) References Cited

OTHER PUBLICATIONS

Srivastava, R. et al., "Phosgene-free synthesis of carbamates over zeolite-based catalyst", Aug. 2004, Catalysis Letters, vol. 97, No. 1-2, pp. 41-47.*
Srivastava, R. et al., "Syntheses of polycarbonate and polyurethane precursors utilizing CO2 over highly efficient solid as-synthesized MCM-41 catalyst", May 9, 2006, Tetrahedron Letters, vol. 47 pp. 4213-4217.*

* cited by examiner

*Primary Examiner*—Yvonne Eyler
*Assistant Examiner*—Yate K Cutliff
(74) *Attorney, Agent, or Firm*—Harold L. Novick; Ari G. Zytcer; The Nath Law Group

(57) ABSTRACT

The present invention provides an improved process for the preparation of carbamates with high selectivity of pharmaceutical interest by an eco-friendly, non-toxic, phosgene-/isocyanate-/CO-free clean route through a reaction of amine, organic halide compound and carbon dioxide in the presence of a solid, reusable catalyst at moderate conditions and does not require additional cocatalyst/promoter as well as solvent.

7 Claims, No Drawings

PROCESS FOR THE PREPARATION OF CARBAMATES

FIELD OF THE INVENTION

The present invention relates to an improved process for the preparation of carbamates of general formula, $R_1NHC(O)OR_2$ wherein, $R_1$=alkyl or aryl having 1-12 carbon atoms, $R_2$=alkyl having 1-8 carbon atoms. Particularly, the present invention relates to an improved process for the preparation of carbamates in the presence of an ordered, mesoporous, modified-silica-based-bifunctional catalyst. More particularly, the present invention relates to an efficient, non-toxic, phosgene-/isocyanate-/CO-free clean process. More particularly, it deals with an improved process wherein the reaction is carried out at moderate conditions avoiding use of additional co-catalysts/promoters such as onium salts.

The ordered, mesoporous, modified-silica-based-bifunctional catalyst used in the present process is claimed and described in our co-pending patent application 152NF2005.

BACKGROUND OF THE INVENTION

Carbamates with —NHC(O)O— structural unit are important raw materials for a variety of polymers (e.g., polyurethanes) used in foams, coatings, adhesives, plastics and fibers. They find application as herbicides, fungicides and pesticides in agrochemical industry (e.g., CARBARYL, CARBOFURAN, PROPOXUR, DIOXACARB, AMINOCARB etc.) and drug intermediates in pharmaceutical industry (e.g., secondary amyl carbamate, trichloroethyl carbamate, physostigmine, carbachol etc.).

Carbamates are conventionally produced by phosgene/isocyanate technology wherein aromatic or aliphatic amine is reacted with phosgene, which is then treated with an alcohol to obtain the corresponding carbamates. This process using phosgene and isocyanate is highly toxic and hence, unsafe. Another incentive to eliminate phosgene is the economic penalty incurred because the chlorine content of phosgene is wasted and converted into NaCl. Caustic soda is consumed in the conversion and the disposal of waste salt solutions presents ecological problems in itself.

Production of carbamates by reductive carbonylation route using noble metal catalysts is another alternative but it is economically not viable; only one-third of CO could be utilized effectively and the separation of CO and $CO_2$ increases the operation cost.

U.S. Pat. No. 5,502,241 which deals with the preparation of alkyl carbamates in particular methyl methyl carbamates by reacting methyl amine or N,N' dimethyl urea with CO, an oxidizing agent and a mono alcohol in the presence of a platinum-based catalyst and a quaternary ammonium halide as a promoter. U.S. Pat. Nos. 4,304,922; 4,297,560; 5,194,660 and 5,502,241 also describe the above said oxidative carbonylation route. High yields of carbamates are achieved with this route. But the method of preparation is hazardous as it involves handling of $CO+O_2$/air mixtures at harsh conditions (50-400 bar; 443 K). Eco-friendly routes for the preparation of carbamates are, therefore, highly desirable.

Methoxycarbonylation of amines using dimethyl carbonate (DMC) as methoxylating agent was proposed as a phosgene-free route (Tetrahedron Letters Year 1986, Vol. 27 page 5521). However, separation of methanol-DMC azeotrope is an expensive operation in this process.

Carbamates can also be synthesized by the Hoffmann rearrangement of amides, reaction of chloroformates and amines etc (Tetrahedron Letters Year 1997, Vol. 38, 8878; Year 1998, Vol. 39, 3259).

Among the several phosgene-/isocyanate-free alternative routes, reaction of primary amines with $CO_2$ and organic halide is the most promising high yielding route (J. Chem. Soc. Chem. Commun. Year 1994, page. 699; Tetrahedron Year 1992, vol. 48, page 1515; U.S. Pat. Nos. 6,528,678; 6,399,808). In addition to the advantageous feature of not being hazardous, the synthetic route contributes to the issue of utilization of "greenhouse effect gas" $CO_2$ and environmental-clean-up. Generally, strong organic bases, crown ethers and onium salts in homogeneous phase stabilize the carbamate anion and catalyze the synthesis of carbamates (Chem. Rev. 2004; J. Org. Chem. Year 1995, vol. 60, 2820). There have been reports on the use of ionic liquids and solids like $CsCO_3$ and $K_2CO_3$ for this reaction as catalysts (Tetrahedron Year 2002, Vol. 58, page 3329; J. Org. Chem. Year 2001; Vol. 66, page. 1035; Organic Letters Year 2000, Vol. 2, page 2797). However, due to their low activity very large amounts of such catalysts (almost equal to the quantity of the substrate) had to be used at long reaction times. Moreover these catalysts require large amounts of quaternary ammonium salt promoters to enhance carbamation while suppressing N-alkylation (U.S. Pat. No. 6,399,808). Other reports that deal with the synthesis of organic carbamates include U.S. Pat. No. 6,566,533 (describing the production of heterocyclic carbamates from aza-heterocycle compound from carbon dioxide); U.S. Pat. No. 5,688,988 (dealing with a process for the production of aromatic urethane by reacting aromatic amines and organic carbonates in presence of Zn and/or copper carbonates/hydroxide); U.S. Pat. No. 4,156,784 (describing carbamates manufacturing by reaction of alcohols with urea in prescence of ion exchangers containing Ni) and U.S. Pat. No. 4,415,745 (describing a process for preparation of aromatic carbamates from isocyanates).

Recently, Srivastava et al., reported the use of titanosilicate molecular sieves and zeolite-encapsulated metal phthalocyanine complexes for this reaction (Srivastava et al. Catal. Lett. Vol. 97, Year 2004, pp. 41-47). Although these catalysts could be reused in recycling experiments high yields of carbamates could be obtained only when solvents like N,N-dimethyl formamide are used in the reaction.

The present invention is a "green" process carried out in the presence of a solid catalyst at moderate temperatures and $CO_2$ pressures. The catalyst could be separated easily by simple filtration and reused. Most importantly, the catalyst is highly efficient and only a small amount of it is needed unlike the prior art solid catalysts. The present invention utilizes an ordered, mesoporous, modified-silica-based bifunctional catalyst;

Mesoporous silica surface is modified with a Lewis acid metal ion preferably tetrahedral $Ti^{4+}$ ions (by grafting) as well as with organic base preferably adenine (by anchoring). Site isolation and synergism between the Lewis acid metal ion and anchored organic base is the major cause for the superior activity of the catalyst of present invention. It has been observed that the solid catalyst of the present invention exhibits good activity with high carbamate selectivity even in the absence of a solvent.

OBJECTIVES OF THE INVENTION

One of the object of the present invention to provide an improved process for preparing carbamates with high selectivity of nearly 80-90 mol % and obviating the drawbacks of the prior art processes.

Another object is to provide a process for the production of carbamates wherein use of toxic phosgene, isocyanate and CO is eliminated. Carbamates are prepared by reacting amine, organic halide and carbon dioxide in the presence of solid modified silica-based catalyst at mild conditions.

Yet another object of the present invention is to eliminate the use of solvent and additional co-catalyst/promoters usually used in the prior-art processes.

SUMMARY OF THE INVENTION

Accordingly the present invention relates to an improved process for the preparation of carbamates, the said process comprising:

reacting amine and alkyl halide in presence of a solid catalyst, in an autoclave, under $CO_2$ pressure of about 3.4 bar at a temperature of about 80° C. for a period of about 4 hours cooling the above said reaction mixture to a temperature of about 25° C. and removing the unreacted carbon dioxide, followed by separation of the catalyst by filtration to obtain the desired product.

In an embodiment of the present invention the amine used is selected from the group consisting of aniline, trimethyl aniline, benzylamine, cyclohexamine, hexylamine and octylamine.

In another embodiment the alkyl halide used is selected from n-butyl bromide, n-hexyl bromide, n-butyl chloride and n-hexyl chloride.

In yet another embodiment the solid catalyst used in step (a) is a surface modified mesoporous silica.

In yet another embodiment of the invention the catalyst mesoporous silica used is having molar composition:

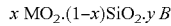
$x\, MO_2.(1-x)SiO_2.y\, B$ wherein, x lies between 0.0095 and 0.025 moles,
y varies between 0.054 and 0.12,
B is adenine,
M is $Ti^{4+}$ ions In yet another embodiment the molar ratio of amine to alkyl halide is in the range of 0.08:1 to 0.85:1.

In yet another embodiment the catalyst used is in the range of 10 mg/mmol to 15 mg/mmol.

In yet another embodiment of the invention the carbamates obtained is selected from the group consisting of butyl-N-phenyl carbamate, butyl-N-2,4,6-trimethyl phenyl carbamate, butyl-N-2,4,6-trimethyl phenyl carbamate, butyl-N-methyl phenyl carbamate, butyl-N-cyclohexyl carbamate and butyl-N-hexyl carbamate.

In yet another embodiment the conversion of amine to carbamates is in the range of 74.5 to 100%.

In yet another embodiment of the invention the selectivity of the desired carbamates obtained is in the range of 76.0 to 95%.

DETAILED DESCRIPTION OF THE INVENTION

In the investigations leading to the present invention, it was found that when the ordered mesoporous silica-surface is modified with both Lewis acid metal ions as well as with organic base the activity and carbamate selectity are enhanced. The prior art catalysts are not sufficiently active as the catalysts of the present invention. The novel solid catalysts of the present invention could be easily separated from the reaction products by simple filtration process, thereby avoids the tedious process of catalyst recovery characteristic of most of the prior art processes. Hence the present invention is environmentally more beneficial. The present invention does not involve the toxic phosgene reactants and hence, unlike the commericial process it is safer. Unlike the prior art catalysts, the reaction using the catalysts of present invention could be carried out without use of any promoters like onium salts.

The preparation of carbamates by an eco-friendly, non-toxic, phosgene-/isocyanate-/CO-free clean route through a reaction of amine, organic halide compound and carbon dioxide in the presence of a solid, reusable catalyst at moderate conditions. The novelty of the present invention is that it is not only highly efficient but requires no additional cocatalyst/promoter as well as solvent. Further due to mesoporosity of the solid catalyst system organic transformations involving bulkier molecules that are of pharmaceutical are also possible. The present process is non-toxic and more atom-efficient leading to economic benefits.

The present invention provides an improved process for preparing carbamates of general formula, $R_1NHC(O)OR_2$; $R_1$=alkyl or aryl having 1-12 carbon atoms and $R_2$=alkyl having 1-8 carbon atoms, which comprises contacting an amine, an organic halide and carbon dioxide at a pressure of 1-4 bar, temperature in the range of 80°-100° C., for period of 2-10 hrs, in the presence of an ordered, mesoporous, modified-silica-based-bifunctional catalyst, and separating of the catalyst for further reuse in recycling experiments and isolation of the carbamate formed from the reaction mixture by conventional methods.

In one of the embodiments of the present invention, the solid catalyst is surface-modified mesoporous silica both with Lewis acid metal ions (M) such as $Ti^{4+}$ ions (by grafting) and organic bases (B) such as adenine (by anchoring) having molar composition:

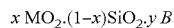
$x\, MO_2.(1-x)SiO_2.y\, B$ wherein, x lies between 0.0095 and 0.025 moles and y varies between 0.054 and 0.12, the process of preparation of which has been claimed and described in a co-pending application U.S. application Ser. No. 11/438,388 and physico-chemical characteristics and fingureprint features as shown in Table-1.

TABLE 1

| | |
|---|---|
| XRD Peaks (degrees) | 0.88, 1.5, 1.7 |
| Space group | p6mm, 2D hexagonal |
| Unit cell parameter | 11.7 nm |
| Interplanar spacing $d_{100}$ (from XRD) | 10 nm |
| Surface area | 627 $m^2/g$ |
| Total pore volume | 1.04 $cm^3/g$ |
| Mesopore volume | 0.96 $cm^3/g$ |
| Micropore volume | 0.08 $cm^3/g$ |
| Pore diameter | 6.7 nm |
| $SiO_2/TiO_2$ (molar ratio) | 40 |
| $SiO_2$/Adenine (molar ratio) | 0.0183 |
| $CO_2$ adsorption (from temperature programmed desorption in the range 298-523 K) | 5.3 mmol per g of catalyst |
| $NH_3$ adsorption (from temperature programmed desorption in the range 323-623 K) | 1 mmol per g of catalyst |
| FT-IR band for covalently anchored Adenine | 3300 $cm^{-1}$ |

TABLE 1-continued

| | |
|---|---|
| Diffuse reflectance UV-visible band for covalently anchored adenine | 266 nm (asymmetric) |
| Diffuse reflectance UV-visible band for dispersed tetrahedral $Ti^{4+}$ ions | 211 nm |

In the present invention the organic base adenine is anchored to the silica surface through a spacer group preferably propyl group, the amine is aniline, 2,4,6-trimethylaniline, benzylamine, cyclohexylamine, hexylamine or octylamine, the organic alkyl halide is n-butyl bromide, amine to Lewis acid molar ratio varies from 220-600, amine to organic base molar ratio varies from 40-100, the ratio of organic halide to amine varies from 0.5 to 1.5, phosgene-/-isocyanate-/CO-free and hence, more environmental-friendly. The process that carbamates are synthesized without using a solvent. It is yet another feature of the process that additional co-catalyst or promoters like onium and phosphonium salts are eliminated. The solid catalyst could be easily separated by simple filtration and could be reused with little loss in activity. In still yet another feature, the selectivity for the carbamate is about 76.0-95%. In still yet another feature of the process that bulkier organic carbamates of pharmaceutical interest can be prepared over the catalysts of present invention.

This process of the present invention is described herein below with reference to the examples, which are illustrative only and should not be construed to limit the scope of the present invention in any manner.

EXAMPLE 1

This example illustrates the preparation of the catalyst of the present invention that contains both the Lewis acid Ti and organic base adenine. In the preparation of the catalyst of the present invention, first mesoporous silica SBA-15 was prepared according to following procedure. In a typical synthesis, 2 g of amphiphilic triblock copolymer, poly(ethylene glycol)-block-poly(propylene glycol)-block-poly(ethylene glycol) ($EO_{20}PO_{70}EO_{20}$; average molecular weight=5800, Aldrich Co.), was dispersed in 15 g of water and 60 g of 2 M HCl solution while stirring, followed by the addition of 4.25 g of tetraethyl orthosilicate (TEOS, Aldrich Co.) to the homogeneous solution. This gel was continuously stirred at 40° C. for 24 h, and finally crystallized in a Teflon-lined steel autoclave at 100° C. for 2 days. After crystallization, the solid product was centrifuged, filtered, washed with deionized water, and dried in air at room temperature (25° C.). The material was calcined at 550° C. for 6 h to decompose the triblock copolymer and obtain a white powder SBA-15. It was then titanated as per the following procedure. In a typical preparation, a certain amount of TBOT was hydrolyzed in 40 mL of glycerol (99 wt %, s. d. fine Chem. Ltd.) containing 7.5 mL of tetrapropylammonium hydroxide (TPAOH; 20 wt %, Aldrich Co.), to obtain a homogeneous solution. To this solution was added 2 g of SBA-15 without any pretreatment, and the mixture was heated statically at 100° C. for 72 h to induce titanation. Ti-SBA-15, thus obtained, was filtered, washed with deionized water, and the organic species were burnt off at 500° C. for 4 h. Titanated mesoporous silica referred as Ti-SBA-15 contains a final Si/Ti molar composition of 40. Organofunctionalization of titanated mesoporous silica (Ti-SBA-15) with done as follows: Ti-SBA-15 was activated under vacuum at 150° C. for about 3 h. To it, 3-chloropropyltriethoxysilane (9 mmol per 3 g of silica support; Lancaster) in 100 ml of dry toluene was added and refluxed under nitrogen for 6 h. Soxhlet extraction with dichlomethane (for 12 h) and then with acetone (for 12 h) yielded propylchloride-functionalized Ti-SBA-15 material (Ti-SBA-15-pr-Cl). This was then condensed with adenine to get adenine functionalized Ti-SBA-15 (referred as Ti-SBA-15-pr-Ade). In a typical condensation procedure, adenine (1.76 mmol, 0.238 g) was taken in 30 ml of dry DMF and stirred for 30 min under nitrogen environment at 120° C. for complete dissolution. Then, 1.5 g of Ti-SBA-15-pr-Cl was added and stirring was continued for 12 h. The solid was filtered, Soxhlet extracted with DMF (for 10 h) and then with $CH_3CN$ (for 12 h).

EXAMPLE 2

This example illustrates the preparation of mesoporous silica SBA-15 modified only with organic base adenine (hereafter referred as SBA-15-pr-Ade). Initially, SBA-15 prepared as reported in EXAMPLE 1 and then it was activated under vacuum at 423 K for about 3 h. To it, 3-chloropropyltriethoxysilane (9 mmol per 3 g of silica SBA-15; Lancaster) in 100 ml of dry toluene was added and refluxed under nitrogen for 6 h. Soxhlet extraction with dichlomethane (for 12 h) and then with acetone (for 12 h) yielded propylchloride-functionalized SBA-15 (hereafter referred as SBA-15-pr-Cl). This was then condensed with adenine to get adenine functionalized SBA-15 (referred as SBA-15-pr-Ade). In a typical condensation procedure, adenine (1.76 mmol, 0.238 g) was taken in 30 ml of dry DMF and stirred for 30 min under nitrogen environment at 393 K for complete dissolution. Then, 1.5 g of SBA-15-pr-Cl was added and stirring was continued for 12 h. The solid was filtered, Soxhlet extracted with DMF (for 10 h) and then with $CH_3CN$ (for 12 h).

EXAMPLE 3

This example illustrates the preparation of butyl-N-phenyl carbamate over SBA-15-pr-Ade catalyst. In a typical reaction, aniline (10 mmol), n-butyl bromide (12 mmol) and catalyst SBA-15-pr-Ade (100 mg; Adenine content=1.29 mmol per g of catalyst) were charged into a 300 ml stainless steel PARR autoclave. The reactor was then pressurized with $CO_2$ (3.4 bar). Temperature was raised to 80° C. and reaction was conducted for 4 h. The reactor was then cooled to 25° C. and unutilized $CO_2$ was vented out. Catalyst was recovered from the reaction mixture by filtration. The products were diluted with dichloromethane and analyzed by thin layer chromatography (TLC) and gas chromatography (Shimadzu 14B GC; SE-52 packed column (6-feet long×1.25-mm i.d.)). They were characterized and identified by GC-MS (Shimadzu QP-5000 (30-m long×0.25-mm i.d.)), FT-IR (Shimadzu 8201 PC spectrophotometer) and $^1H$ NMR (Bruker AC 200) spectroscopies. Mass balance was >98%.

EXAMPLE 4

This example illustrates the preparation of butyl-N-phenyl carbamate over Ti-SBA-15 catalyst. In a typical reaction, aniline (10 mmol), n-butyl bromide (12 mmol) and catalyst Ti-SBA-15 (100 mg; Si/Ti molar ratio=40) were charged into a 300 ml stainless steel PARR autoclave. The reactor was then pressurized with $CO_2$ (3.4 bar). Temperature was raised to 80° C. and reaction was conducted for 4 h. The reactor was then cooled to 25° C. and unutilized $CO_2$ was vented out. The catalyst was recovered from the reaction mixture by filtration. The products were diluted with dichloromethane and analyzed by thin layer chromatography (TLC) and gas chromatography (Shimadzu 14B GC; SE-52 packed column (6-feet long×1.25-mm i.d.)). They were characterized and identified by GC-MS (Shimadzu QP-5000 (30-m long×0.25-mm i.d.)), FT-IR (Shimadzu 8201 PC spectrophotometer) and $^1$H NMR (Bruker AC 200) spectroscopies. Mass balance was >98%.

EXAMPLE 5

This example illustrates the preparation of butyl-N-phenyl carbamate over both Lewis acid and organic base containing solid silica catalysts, Ti-SBA-15-pr-Ade. In a typical reaction, aniline (10 mmol), n-butyl bromide (12 mmol) and catalyst Ti-SBA-15-pr-Ade (100 mg; Si/Ti molar ratio=40; Ademine content=0.91 mmol per gram catalyst) were charged into a 300 ml stainless steel PARR autoclave. The reactor was then pressurized with $CO_2$ (3.4 bar). Temperature was raised to 80° C. and reactions was conducted for 4 h. The reactor was then cooled to 25° C. and unutilized $CO_2$ was vented out. The catalyst was recovered from the reaction mixture by filtration. The products were diluted with dichloromethane and analyzed by thin layer chromatography (TLC) and gas chromatography (Shimadzu 14B GC; SE-52 packed column (6-feet long×1.25-mm i.d.)). They were characterized and identified by GC-MS (Shimadzu QP-5000 (30-m long×0.25-mm i.d.)), FT-IR (Shimadzu 8201 PC spectrophotometer) and $^1$H NMR (Bruker AC 200) spectroscopies. Mass balance was >98%.

EXAMPLE 6

This example illustrates the preparation of bulkier carbamate, butyl-N-2,4,6-trimethyl phenyl carbamate, for example over SBA-15-pr-Ade. In a typical reaction, 2,4,6-trimethyl aniline (10 mmol), n-butyl bromide (12 mmol) and catalyst SBA-15-pr-Ade (100 mg; 1.29 mmol per g catalyst) were charged into a 300 ml stainless steel PARR autoclave. The reactor was then pressurized with $CO_2$ (3.4 bar). Temperature was raised to 80° C. and reactions was conducted for 4 h. The reactor was then cooled to 25° C. and unutilized $CO_2$ was vented out. The catalyst was recovered from the reaction mixture by filtration. The products were diluted with dichloromethane and analyzed by thin layer chromatography (TLC) and gas chromatography (Shimadzu 14B GC; SE-52 packed column (6-feet long×1.25-mm i.d.)). They were characterized and identified by GC-MS (Shimadzu QP-5000 (30-m long×0.25-mm i.d.)), FT-IR (Shimadzu 8201 PC spectrophotometer) and $^1$H NMR (Bruker AC 200) spectroscopies.

EXAMPLE 7

This example illustrates the preparation of bulkier carbamate, butyl-N-2,4,6-trimethyl phenyl carbamate, for example, over Ti-SBA-15 catalyst. In a typical reaction, 2,4,6-trimethyl aniline (10 mmol), n-butyl bromide (12 mmol) and catalyst Ti-SBA-15-(100 mg; Si/Ti molar ratio=40) were charged into a 300 ml stainless steel PARR autoclave. The reactor was then pressurized with $CO_2$ (3.4 bar). Temperature was raised to 80° C. and reaction was conducted for 4 h. The reactor was then cooled to 25° C. and unutilized $CO_2$ was vented out. The catalyst was recovered from the reaction mixture by filtration. The products were diluted with dichloromethane and analyzed by thin layer chromatography (TLC) and gas chromatography (Shimadzu 14B GC; SE-52 packed column (6-feet long×1.25-mm i.d.)). They were characterized and identified by GC-MS (Shimadzu QP-5000 (30-m long×0.25-mm i.d.)), FT-IR (Shimadzu 8201 PC spectrophotometer) and $^1$H NMR (Bruker AC 200) spectroscopies.

EXAMPLE 8

This example illustrates the preparation of bulkier carbamate, butyl-N-2,4,6-trimethyl phenyl carbamate over Ti-SBA-15-pr-Ade catalyst. In a typical reaction, 2,4,6-trimethyl aniline (10 mmol), n-butyl bromide (12 mmol) and catalyst Ti-SBA-15-pr-Ade (100 mg; Si/Ti=40 and Adenine content=0.91 mmol/g catalyst) were charged into a 300 ml stainless steel PARR autoclave. The reactor was then pressurized with $CO_2$ (3.4 bar). Temperature was raised to 80° C. and reaction was conducted for 4 h. The reactor was then cooled to 25° C. and unutilized $CO_2$ was vented out. The catalyst was recovered from the reaction mixture by filtration. The products were diluted with dichloromethane and analyzed by thin layer chromatography (TLC) and gas chromatography (Shimadzu 14B GC; SE-52 packed column (6-feet long×1.25-mm i.d.)). They were characterized and identified by GC-MS (Shimadzu QP-5000 (30-m long×0.25-mm i.d.)), FT-IR (Shimadzu 8201 PC spectrophotometer) and $^1$H NMR (Bruker AC 200) spectroscopies.

EXAMPLE 9

This example illustrates the preparation of butyl-N-methyl phenyl carbamate over SBA-15-pr-Ade. In a typical reaction, benzylamine (10 mmol), n-butyl bromide (12 mmol) and catalyst SBA-15-pr-Ade (100 mg; Adenine content=1.29 mmol/g) were charged into a 300 ml stainless steel PARR autoclave. The reactor was then pressurized with $CO_2$ (3.4 bar). Temperature was raised to 80° C. and reaction was conducted for 4 h. The reactor was then cooled to 25° C. and unutilized $CO_2$ was vented out. The catalyst was recovered from the reaction mixture by filtration. The products were identified and quantified as above.

EXAMPLE 10

This example illustrates the preparation of butyl-N-methyl phenyl carbamate over Ti-SBA-15-pr-Ade. In a typical reaction, benzylamine (10 mmol), n-butyl bromide (12 mmol) and catalyst Ti-SBA-15-pr-Ade (100 mg; Si/Ti mole=40; Adenine content=0.91 mmol/g) were charged into a 300 ml stainless steel PARR autoclave. The reactor was then pressurized with $CO_2$ (3.4 bar). Temperature was raised to 80° C. and reaction was conducted for 4 h. The reactor was then cooled to 25° C. and unutilized $CO_2$ was vented out. The catalyst was recovered from the reaction mixture by filtration. The products were identified and quantified as above.

EXAMPLE 11

This example illustrates the preparation of butyl-N-cyclohexyl carbamate over SBA-15-pr-Ade. In a typical reaction, cyclohexylamine (10 mmol), n-butyl bromide (12 mmol) and catalyst SBA-15-pr-Ade (100 mg; Adenine content=1.29 mmol/g catalyst) were charged into a 300 ml stainless steel PARR autoclave. The reactor was then pressurized with $CO_2$ (3.4 bar). Temperature was raised to 80° C. and reaction was conducted for 4 h. The reactor was then cooled to 25° C. and unutilized $CO_2$ was vented out. The catalyst was recovered from the reaction mixture by filtration. The products were identified and quantified as above.

EXAMPLE 12

This example illustrates the preparation of butyl-N-hexyl carbamate over SBA-15-pr-Ade. In a typical reaction, hexylamine (10 mmol), n-butyl bromide (12 mmol) and catalyst SBA-15-pr-Ade (100 mg; Adenine content=1.2 mmol/g catalyst) were charged into a 300 ml stainless steel PARR autoclave. The reactor was then pressurized with $CO_2$ (3.4 bar). Temperature was raised to 80° C. and reaction was conducted for 4 h. The reactor was then cooled to 25° C. and unutilized $CO_2$ was vented out. The catalyst was recovered from the reaction mixture by filtration. The products were identified and quantified as above.

EXAMPLE 13

This example illustrates the preparation of butyl-N-octyl carbamate over SBA-15-pr-Ade. In a typical reaction, octylamine (10 mmol), n-butyl bromide (12 mmol) and catalyst SBA-15-pr-Ade (100 mg; Adenine content=1.29 mmol/g catalyst) were charged into a 300 ml stainless steel PARR autoclave. The reactor was then pressurized with $CO_2$ (3.4 bar). Temperature was raised to 80° C. and reactions were conducted for 4 h. The reactor was then cooled to 25° C. and unutilized $CO_2$ was vented out. The catalyst was recovered from the reaction mixture by filtration. The products were identified and quantified as above.

EXAMPLE 14

This example illustrate the recyalability of Ti-SBA-15-pr-Ade catalyst in the synthesis of butyl-N-phenyl carbamate. The used catalyst in Example 5 was washed with acetonitrile and then with acetone and then dried at 383 K for 1 hr. This washed catalyst was used in the recycle experiment. In a typical reaction, aniline (10 mmol), n-butyl bromide (12 mmol) and used catalyst Ti-SBA-15-pr-Ade (100 mg; Si/Ti=40) were charged into a 300 ml stainless steel PARR autoclave. The reaction was conducted in the same manner as described in Example 5 and the products were isolated and analyzed. The catalyst was recycled three times in a similar manner.

Catalytic activity data of different catalysts and products selectivity are listed in Table 2.

catalyst and the separated catalysts can be reused. High selectivity for carbamate can be obtained without using any additional co-catalysts or promoters.

We claim:

1. An improved process for the preparation of carbamates, which comprises reacting amine and alkyl halide in presence of an ordered, bi-functional mesoporous silica catalyst with a molar composition of:

$$X\, MO_2. (1-x)\, SiO_2.y\, B$$

wherein B is adenine, M is $Ti^{4+}$ ions, x lies between 0.0095 and 0.025 moles; y varies between 0.054 and 0.12 moles, and wherein said reacting is in an autoclave, under $CO_2$ pressure of about 3.4 bar, at a temperature of about 80° C., for a period of about 4 hours cooling the above said reaction mixture to a temperature of about 25° C. and removing the unreacted $CO_2$, followed by the separation of the catalyst by filtration to obtain the desired product.

2. An improved process as claimed in claim 1, wherein the amine used is selected from the group consisting of aniline, trimethyl aniline, benzylamine, cyclohexamine, hexylamine and octylamine.

3. An improved process as claimed in claim 1, wherein the alkyl halide used is selected from n-butyl bromide, n-hexyl bromide, n-butyl chloride and n-hexyl chloride.

4. An improved process as claimed in claim 1, wherein the molar ratio of amine to alkyl halide is in the range of 0.08:1 to 0.85:1.

5. An improved process as claimed in claim 1, wherein the catalyst used is in the range of 10 mg/mmol to 15 mg/mmol.

6. An improved process as claimed in claim 1, wherein carbamates obtained is selected from the group consisting of butyl-N-phenyl carbamate, butyl-N-2,4,6-trimethyl phenyl carbamate, butyl-N-2,4,6-trimethyl phenyl carbamate, butyl-N-methyl phenyl carbamate, and butyl-N-cyclohexyl carbamate and butyl-N-hexyl carbamate.

TABLE 2

| Example No. | Catalyst | Amine | Amine conversion (wt %) | Carbamate selectivity[a] % |
|---|---|---|---|---|
| 3 | SBA-15-pr-Ade | Aniline | 44.2 | 87.3 |
| 4 | Ti-SBA-15 | Aniline | 48.1 | 79.1 |
| 5 | Ti-SBA-15-pr-Ade | Aniline | 100 | 89.0 |
| 6. | SBA-15-pr-Ade | 2,4,6 trimethylaniline | 32.5 | 93.5 |
| 7. | Ti-SBA-15 | 2,4,6 trimethylaniline | 21.8 | 87.4 |
| 8. | Ti-SBA-15-pr-Ade | 2,4,6 trimethylaniline | 74.5 | 87.8 |
| 9. | SBA-15-pr-Ade | Benzylamine | 62.0 | 98.0 |
| 10. | Ti-SBA-15-pr-Ade | Benzylamine | 88.6 | 92.8 |
| 11. | SBA-15-pr-Ade | Cyclohexylamine | 91.0 | 83.5 |
| 12 | SBA-15-pr-Ade | Hexylamine | 96.5 | 88.0 |
| 13 | SBA-15-pr-Ade | Octylamine | 98.8 | 93.5 |
| 14 | Ti-SBA-15-pr-Ade | Aniline | | |
| | Recycle-1 | | 100 | 76.0 |
| | Recycle-2 | | 92.0 | 76.3 |
| | Recycle-3 | | 89.3 | 76.4 |

[a]Balance selectivity is for N-alkylated amine product

The process described above has the combined unique advantages of high conversion of amine accompanied with high selectivity for carbamate. The process is environmental-friendly and does not involve toxic reactants like phosgene, isocyanate and CO. Little efforts are required to separate the 7. An improved process as claimed in claim 1, wherein the selectivity of the desired carbamates obtained is in the range of 76.0 to 95% at an amine conversion in the range of 75.4 to 100%.

* * * * *